US011465131B2

United States Patent
Lee et al.

(10) Patent No.: US 11,465,131 B2
(45) Date of Patent: Oct. 11, 2022

(54) METHOD FOR PRODUCING FERRITE-BASED COATING CATALYST AND METHOD FOR PRODUCING BUTADIENE BY USING SAME

(71) Applicant: LG Chem, LTD., Seoul (KR)

(72) Inventors: Joohyuck Lee, Daejeon (KR); Dong Hyun Ko, Daejeon (KR); Kyong Yong Cha, Daejeon (KR); Myungji Suh, Daejeon (KR)

(73) Assignee: LG CHEM, LTD., Seoul (KR)

( * ) Notice: Subject to any disclaimer, the term of this patent is extended or adjusted under 35 U.S.C. 154(b) by 181 days.

(21) Appl. No.: 16/963,161

(22) PCT Filed: Feb. 26, 2019

(86) PCT No.: PCT/KR2019/002313
§ 371 (c)(1),
(2) Date: Jul. 17, 2020

(87) PCT Pub. No.: WO2019/177285
PCT Pub. Date: Sep. 19, 2019

(65) Prior Publication Data
US 2021/0114001 A1    Apr. 22, 2021

(30) Foreign Application Priority Data

Mar. 13, 2018   (KR) .................. 10-2018-0029258

(51) Int. Cl.
*B01J 21/04* (2006.01)
*B01J 23/80* (2006.01)
(Continued)

(52) U.S. Cl.
CPC ............... *B01J 23/80* (2013.01); *B01J 21/04* (2013.01); *B01J 31/061* (2013.01); *B01J 31/28* (2013.01);
(Continued)

(58) Field of Classification Search
CPC ........ B01J 23/005; B01J 23/76; B01J 23/745; B01J 23/04; C07C 11/167; C07C 2523/76; C07C 2523/745
See application file for complete search history.

(56) References Cited

U.S. PATENT DOCUMENTS

| 4,058,577 A | 11/1977 | Baker |
| 9,550,174 B2 | 1/2017 | Kwon et al. |

(Continued)

FOREIGN PATENT DOCUMENTS

| CN | 103381366 | 11/2013 |
| EP | 3222347 A1 | 9/2017 |

(Continued)

OTHER PUBLICATIONS

Machine Translation of KR101340620B1 (Year: 2013).*

*Primary Examiner* — Ellen M Mcavoy
*Assistant Examiner* — Ming Cheung Po
(74) *Attorney, Agent, or Firm* — Dentons US LLP

(57) ABSTRACT

The method for preparing a ferrite-based coating catalyst including mixing a support, a ferrite-based catalyst, a cellulose-based additive, and water, in which a content of the cellulose-based additive is 0.5 wt % or less based on a total weight of the ferrite-based catalyst.

12 Claims, 1 Drawing Sheet

(51) Int. Cl.
- *B01J 31/06* (2006.01)
- *B01J 31/28* (2006.01)
- *B01J 37/02* (2006.01)
- *C07C 5/48* (2006.01)

(52) U.S. Cl.
CPC ....... *B01J 37/0219* (2013.01); *B01J 37/0223* (2013.01); *C07C 5/48* (2013.01); *B01J 2231/766* (2013.01); *B01J 2531/007* (2013.01); *C07C 2521/04* (2013.01); *C07C 2523/80* (2013.01)

(56) References Cited

U.S. PATENT DOCUMENTS

| | | |
|---|---|---|
| 9,604,199 B2 | 3/2017 | Hiraoka et al. |
| 2011/0105818 A1 | 5/2011 | Pelati et al. |
| 2013/0158325 A1 | 6/2013 | Kwon et al. |
| 2015/0165432 A1 | 6/2015 | Rui et al. |
| 2018/0186711 A1 | 7/2018 | Suh et al. |
| 2019/0016649 A1 | 1/2019 | Kim et al. |

FOREIGN PATENT DOCUMENTS

| | | | |
|---|---|---|---|
| JP | 2004-136267 | 5/2004 | |
| JP | 2007-111581 | 5/2007 | |
| JP | 2013-536066 | 9/2013 | |
| KR | 10-2012-0009687 | 2/2012 | |
| KR | 10-1340620 | 12/2013 | |
| KR | 101340620 B1 * | 12/2013 | ............. B01J 23/76 |
| KR | 10-2014-0082869 | 7/2014 | |
| KR | 10-2015-0036205 | 4/2015 | |
| KR | 10-2017-0119051 | 10/2017 | |
| KR | 10-1854434 | 5/2018 | |
| WO | 2013-161702 | 10/2013 | |
| WO | 2019-013473 | 1/2019 | |

\* cited by examiner

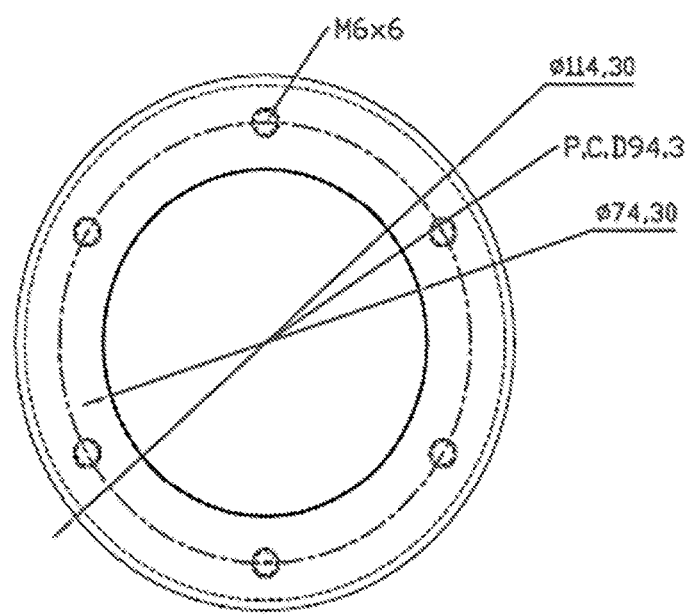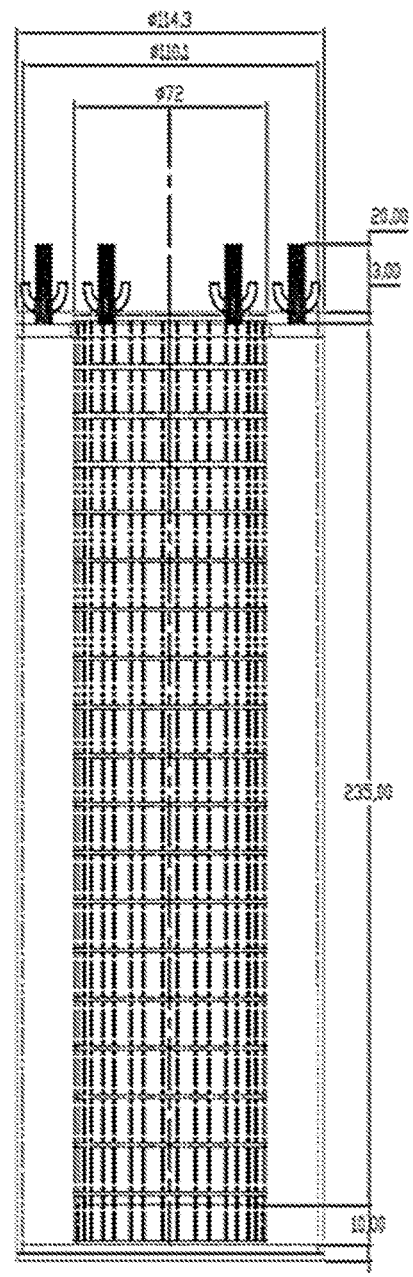

METHOD FOR PRODUCING FERRITE-BASED COATING CATALYST AND METHOD FOR PRODUCING BUTADIENE BY USING SAME

This application is a National Stage Application of International Application No. PCT/KR2019/002313 filed on Feb. 26, 2019, which claims priority to and the benefit of Korean Patent Application No. 10-2018-0029258 filed in the Korean Intellectual Property Office on Mar. 13, 2018, the entire contents of which are incorporated herein by reference.

TECHNICAL FIELD

The present application relates to a method for preparing a ferrite-based coating catalyst and a method for preparing butadiene using the same.

BACKGROUND 1,3-butadiene is one of the main fundamental oil components whose prices fluctuate rapidly while being linked to supply and demand situations of the petrochemical industry as a representative raw material of synthetic rubber. Examples of a method for preparing 1,3-butadiene comprise naphtha cracking, a direct dehydrogenation reaction of normal-butene, an oxidative dehydrogenation reaction of normal-butene, and the like. The oxidative dehydrogenation reaction of normal-butene is a reaction in which butene and oxygen react with each other in the presence of a metal oxide catalyst to produce 1,3-butadiene and water, and has a very thermodynamically favorable advantage because stable water is produced. Further, there are advantages in that it is possible to reduce energy and obtain 1,3-butadiene with high yield because the oxidative dehydrogenation reaction of normal-butene is an exothermic reaction unlike the direct dehydrogenation reaction, so that the reaction process is operated at a relatively low temperature, and the oxidative dehydrogenation reaction is very suitable as a commercialized process because carbon deposits which shorten the lifetime of a catalyst by adding an oxidant to poison the catalyst are less produced and the carbon deposits are easily removed.

However, many side reactions such as a complete oxidation reaction are expected because oxygen is used as a reactant in the oxidative dehydrogenation reaction, and as a result, it is the most important core technology to suppress such side reactions as much as possible and develop catalysts having high selectivity of 1,3-butadiene.

Among metal oxide catalysts used in an oxidative dehydrogenation reaction of normal-butene known so far, ferrite-based catalysts are known as being excellent in activity and stability. However, ferrite-based catalysts have a problem in that the activity or durability thereof deteriorates due to excessive heat generation caused by the reaction conditions of high temperature/high pressure, and furthermore, have a problem in that since a side reaction in which COx is produced is promoted, the amount of heat generated is further increased, so that the selectivity of butadiene is decreased in addition to the deterioration in activity or durability of the catalyst.

In order to solve the problems, technologies of controlling heat generation, such as dissipation of generated heat by mixing inert materials such as an aluminum ball, have been reported, but it is known that the effect of reducing heat generation is insignificant, and particularly, in a bulk reaction where the amount of butadiene produced is considerable, it is more difficult to control heat generation of ferrite-based catalysts. In addition, a phenomenon in which the activity rather deteriorates as an additive is introduced is also discovered.

Therefore, there is an urgent need for developing a method for preparing a catalyst capable of improving the physical strength of the catalyst without affecting the selectivity or yield of butadiene under high temperature and high pressure reaction conditions.

Technical Problem

The present application has been made in an effort to provide a method for preparing a ferrite-based coating catalyst and a method for preparing butadiene using the same.

In particular, an object of the present application is to provide a coating catalyst for an oxidative dehydrogenation reaction capable of more effectively controlling heat generation when the coating catalyst is used for a commercialized reaction in which the amount of butadiene produced is equal to or more than the amount at the laboratory level, and a preparation method thereof.

Further, an object of the present application is to provide a preparation method which improves the physical strength of the catalyst while maintaining the yield or selectivity of butadiene by using the coating catalyst.

The object and other objects of the present application can be all achieved by the detailed description of the present application to be described below.

Technical Solution

An exemplary embodiment of the present application provides a method for preparing a ferrite-based coating catalyst, the method comprising:

mixing a support, a ferrite-based catalyst, a cellulose-based additive, and water, in which a content of the cellulose-based additive is 0.5 wt % or less based on a total weight of the ferrite-based catalyst.

In addition, another exemplary embodiment of the present application provides a method for preparing butadiene, the method comprising:

preparing a ferrite-based coating catalyst prepared by the preparation method; and preparing butadiene by using the ferrite-based coating catalyst in an oxidative dehydrogenation reaction of butene.

According to an exemplary embodiment of the present application, during the preparation of a ferrite-based coating catalyst, it is possible to improve the strength of the ferrite-based coating catalyst by introducing water and a cellulose-based additive. Accordingly, during the preparation of butadiene using the ferrite-based coating catalyst, it is possible to prevent the loss of the catalyst caused by attrition.

Furthermore, the ferrite-based coating catalyst prepared according to an exemplary embodiment of the present application can improve the catalyst strength while maintaining the catalytic activity.

BRIEF DESCRIPTION OF THE DRAWINGS

FIG. 1 is a view illustrating an attrition test device applied to an Experimental Example of the present application.

DETAILED DESCRIPTION

Hereinafter, the present application will be described in more detail.

In the present specification, the 'yield (%)' is defined as a value obtained by dividing the weight of 1,3-butadiene, which is a product of an oxidative dehydrogenation reaction, by the weight of butene which is a raw material. For example, the yield can be represented by the following equation.

Yield (%)=[(the number of moles of 1,3-butadiene produced)/(the number of moles of butene supplied)]×100

In the present specification, the 'conversion (%)' refers to a rate at which a reactant is converted into a product, and for example, the conversion of butene can be defined by the following equation.

Conversion (%)=[(the number of moles of butene reacting)/(the number of moles of butene supplied)]×100

In the present specification, the 'selectivity (%)' is defined as a value obtained by dividing the change amount of butadiene (BD) by the change amount of butene (BE). For example, the selectivity can be represented by the following equation.

Selectivity (%)=[(the number of moles of 1,3-butadiene or COx produced)/(the number of moles of butene reacting)]×100

Amount of catalyst coated (wt %)=[(mass of ferrite-based catalyst, g)/(mass of support, g+mass of ferrite-based catalyst, g)]×100

Rate of catalyst lost (wt %)=[(mass before attrition experiment, g−mass after attrition experiment, g)/(mass before attrition experiment, g×amount of catalyst coated, wt %)]×100

The present inventors confirmed that when a catalyst was prepared by preparing a metal oxide and coating a support with the metal oxide, the reactivity was excellent and the selectivity of a product was excellent because the surface area of the catalyst per unit volume was large during an oxidative dehydrogenation reaction, thereby completing the present invention based on this finding.

The method for preparing a ferrite-based coating catalyst according to an exemplary embodiment of the present application comprises: mixing a support, a ferrite-based catalyst, a cellulose-based additive, and water, in which a content of the cellulose-based additive is 0.5 wt % or less based on a total weight of the ferrite-based catalyst.

According to an exemplary embodiment of the present application, during the preparation of a ferrite-based coating catalyst, it is possible to improve the strength of the ferrite-based coating catalyst by introducing water and a cellulose-based additive. Accordingly, during the preparation of butadiene using the ferrite-based coating catalyst, it is possible to prevent the loss of the catalyst caused by attrition.

In an exemplary embodiment of the present application, the content of the cellulose-based additive can be 0.5 wt % or less based on the total weight of the ferrite-based catalyst which is introduced during the preparation of the ferrite-based coating catalyst, and is more preferably more than 0 and 0.1 wt % or less. When a cellulose-based additive within a range out of the content is introduced, the catalyst strength is improved, but the catalytic activity deteriorates, which is not preferred.

In an exemplary embodiment of the present application, the cellulose-based additive can comprise one or more of methyl cellulose and hydroxypropylmethylcellulose.

In an exemplary embodiment of the present application, the form of the cellulose-based additive is not particularly limited. For example, the cellulose-based additive can also be used in the form of a powder, and can be used in the form of a liquid mixed with water.

In an exemplary embodiment of the present application, in the mixing of the support, the ferrite-based catalyst, the cellulose-based additive, and the water, the support, the ferrite-based catalyst, and the cellulose-based additive can be mixed, and then the resulting mixture can be mixed with the water. Further, in the mixing of the support, the ferrite-based catalyst, the cellulose-based additive, and the water, the cellulose-based additive and the water can be mixed, and then the resulting mixture can be mixed with the support and the ferrite-based catalyst. In this case, the weight ratio of water based on the weight of the support can be 0.1 or less, and can be 0.01 to 0.1. When the weight ratio satisfies the above-described weight ratio range, it is possible to prepare a ferrite-based coating catalyst with the improved catalyst strength while maintaining the catalytic activity.

In an exemplary embodiment of the present application, the mixing of the support, the ferrite-based catalyst, the cellulose-based additive, and the water can be performed in a coating machine which is a rotating body. The coating machine is not particularly limited, and those known in the art can be used.

In an exemplary embodiment of the present application, the ferrite-based catalyst can be represented by the following Formula 1.

$$AFe_2O_4 \hspace{4em} \text{Formula 1}$$

In Formula 1, A is Cu, Ra, Ba, Sr, Ca, Cu, Be, Zn, Mg, Mn, Co, or Ni.

In an exemplary embodiment of the present application, it is preferred that the ferrite-based catalyst is a zinc ferrite catalyst.

In an exemplary embodiment of the present application, the content of the ferrite-based catalyst in the ferrite-based coating catalyst can be 10 wt % to 40 wt %, and 12 wt % to 35 wt % based on the total weight of the ferrite-based coating catalyst. When the content of the ferrite-based catalyst is less than 10 wt % or more than 40 wt % based on the total weight of the ferrite-based coating catalyst, the effect of improving the catalytic activity is insignificant, and when the content thereof satisfies the above range, it is possible to prepare a ferrite-based coating catalyst with the improved catalyst strength while maintaining the catalytic activity.

In an exemplary embodiment of the present application, the support can comprise one or more of alumina, silica, cordierite, titania, zirconia, silicon nitride, and silicon carbide. In an exemplary embodiment of the present application, it is preferred that the support is alumina.

The form of the support is not particularly limited, and for example, the support can be alumina in the form of a sphere, and in this case, the diameter thereof can be 2 mm to 7 mm.

In an exemplary embodiment of the present application, the method can further comprise drying the resulting mixture after the mixing of the support, the ferrite-based catalyst, the cellulose-based additive, and the water. The method can further comprise firing the mixture after the drying, if necessary. The drying can be performed under the temperature conditions of room temperature, 50° C. to 150° C., 90° C. to 120° C., and the like, but the temperature conditions are not limited thereto.

In an exemplary embodiment of the present application, when the content of water is too small, it is impossible to prepare the coating catalyst, and when the content of water is too large, the support is immersed in water, so that it is impossible to prepare the coating catalyst. In an exemplary embodiment of the present application, the weight ratio of water based on the weight of the support can be 0.1 or less, and can be 0.01 to 0.1. When the weight ratio satisfies the above-described weight ratio range, it is possible to prepare a ferrite-based coating catalyst with the improved catalyst strength while maintaining the catalytic activity.

Methods for preparing a ferrite-based catalyst in the related art typically use a pellet-type catalyst molding method using an extruder. However, the pellet catalyst can adversely affect the reaction activity because the high catalyst density in the pellet decreases heat dissipation. Accordingly, it can be an alternative to coat an alumina ball as an inert support with a catalyst, but this method improves the reaction activity of the catalyst, but can incur difficulties in treatment because the physical strength of the catalyst becomes weak. The reason is that the support is coated with the catalyst by using a small amount of water.

Therefore, other materials can be introduced in the form of an additive in order to improve the physical strength of the catalyst, but even when a material known as being good for improving the strength in the related art is introduced, the material can fail to play a role in a catalyst for producing butadiene, and there can occur a problem in that even when the strength is improved, the reaction activity deteriorates.

The present inventors found that when a cellulose-based additive was applied as an additive, a ferrite-based coating catalyst to be prepared could improve the catalyst strength while maintaining the catalytic activity. In particular, by adjusting the content of the cellulose-based additive to 0.5 wt % or less based on the total weight of the ferrite-based catalyst to be introduced during the preparation of the ferrite-based coating catalyst, it was possible to improve the catalyst strength while maintaining the catalytic activity of the ferrite-based coating catalyst.

Further, an exemplary embodiment of the present application provides a method for preparing butadiene, the method comprising: preparing a ferrite-based coating catalyst prepared by the preparation method; and preparing butadiene by using the ferrite-based coating catalyst in an oxidative dehydrogenation reaction of butene.

The oxidative dehydrogenation reaction means a reaction of producing conjugated diene and water by allowing olefin and oxygen to react with each other in the presence of a ferrite-based coating catalyst, and can be a reaction of producing 1,3-butadiene and water by allowing butene and oxygen to react with each other, as a specific example.

A reactor used in the oxidative dehydrogenation reaction is not particularly limited as long as the reactor can be used in the oxidative dehydrogenation reaction, but as an example, the reactor can be a reactor in which the reaction temperature of a catalyst layer installed therein is constantly maintained and the oxidative dehydrogenation reaction is performed while a reactant successively passes through the catalyst layer, and as a specific example, the reactor can be a tubular reactor, a batch-type reactor, a fluidized bed reactor, or a fixed bed reactor, and an example of the fixed bed reactor can be a multi-tubular reactor or a plate-type reactor.

According to an exemplary embodiment of the present application, the preparing of the butadiene can be performed at a reaction temperature of 250° C. to 450° C., 300° C. to 430° C., or 350° C. to 425° C. by using a raw material comprising C4 fractions, steam, oxygen ($O_2$), and nitrogen ($N_2$), and within the above range, the reaction efficiency is excellent without significantly increasing the energy costs, which makes it possible to provide butadiene with high productivity, and maintain the catalytic activity and stability at high levels.

The oxidative dehydrogenation reaction can be performed at a gas hourly space velocity (GHSV) of 50 $h^{-1}$ to 2,000 $h^{-1}$, 50 $h^{-1}$ to 1,500 $h^{-1}$, or 50 $h^{-1}$ to 1,000 $h^{-1}$ based on normal-butene, as an example, and within the range, the reaction efficiency is excellent, which makes it possible to exhibit effects in that conversion, selectivity, yield, and the like are excellent.

The C4 fractions can mean C4 raffinate-1,2,3 remaining by separating useful compounds from a C4 mixture produced by naphtha cracking, and can mean C4 classes which can be obtained through ethylene dimerization.

According to an exemplary embodiment of the present specification, the C4 fractions can be one or a mixture of two or more selected from the group consisting of n-butane, trans-2-butene, cis-2-butene, and 1-butene.

According to an exemplary embodiment of the present specification, the steam or nitrogen ($N_2$) is a diluted gas introduced for the purpose of reducing the explosion danger of the reactant, preventing coking of the catalyst, removing the reaction heat, and the like, in the oxidative dehydrogenation reaction.

According to an exemplary embodiment of the present specification, the oxygen ($O_2$) is an oxidant and reacts with C4 fractions to cause a dehydrogenation reaction.

According to an exemplary embodiment of the present specification, the oxidative dehydrogenation reaction can proceed according to the following Reaction Formula 1 or Reaction Formula 2.

$$C_4H_8 + \tfrac{1}{2}O_2 \rightarrow C_4H_6 + H_2O \qquad \text{Reaction Formula 1}$$

$$C_4H_{10} + O_2 \rightarrow C_4H_6 + 2H_2O \qquad \text{Reaction Formula 2}$$

Hydrogen of butane or butene is removed by the oxidative dehydrogenation reaction, and as a result, butadiene is prepared. Meanwhile, the oxidative dehydrogenation reaction can produce a side reaction product comprising carbon monoxide (CO), carbon dioxide ($CO_2$), or the like, in addition to the main reaction such as Reaction Formula 1 or 2. The oxidative dehydrogenation reaction can comprise a process in which the side reaction product is separated so as not to be continuously accumulated in the process, and is released out of the system.

According to an exemplary embodiment of the present specification, in the method for preparing butadiene, the conversion of butene can be 72% or more, preferably 72.5% or more, and more preferably 79% or more.

According to an exemplary embodiment of the present specification, in the method for preparing butadiene, the selectivity of butadiene can be 85% or more, preferably 85.8% or more, and more preferably 87% or more.

Exemplary Embodiments

Hereinafter, the present application will be described in detail with reference to Examples for specifically describing the present application. However, the Examples according to the present application can be modified in various forms, and it is not interpreted that the scope of the present application is limited to the Examples described in detail below. The Examples of the present application are provided for more completely explaining the present application to the person with ordinary skill in the art.

EXAMPLES

Example 1

2 L of ammonia water whose pH was adjusted to 8 was prepared, and a metal precursor solution comprising 2 L of distilled water, 288.456 g of zinc chloride ($ZnCl_2$), and 1,132.219 g of iron (III) chloride ($FeCl_3$) was prepared in a separate container. In this case, the molar ratio of the metal components comprised in the metal precursor solution was Fe:Zn=2:1. Ammonia water at a concentration of 9 wt % was together added to the prepared ammonia water in order to maintain the pH to 8 while adding the prepared metal precursor solution to the prepared ammonia water. After the metal precursor solution was completely added while stirring the mixture for 1 hour using a stirrer in order to obtain a sample having the uniform composition, the resulting mixture was aged for 1 hour, and then a solution in which a precipitate was formed was washed by using 4 L of distilled water and simultaneously filtered to separate the precipitate. A co-precipitate was obtained by filtering a co-precipitation solution, which had been thoroughly stirred and aged, under reduced pressure using a vacuum filter, the co-precipitate was washed, and then dried at 90° C. for 24 hours, and then the dried co-precipitate was put into a firing furnace and heat-treated at 650° C. for 6 hours to prepare a zinc ferrite catalyst. A $ZnFe_2O_4$ powder was obtained. The obtained powder was ground and selected by a sieving method so as to have a size of 45 μm or less.

After the ferrite-based catalyst and methyl cellulose were mixed, the resulting mixture, an alumina support in the form of balls having a diameter of 4 mm to 6 mm, and water were introduced together into a coating machine, which is a rotating body, and then mixed to prepare a ferrite-based coating catalyst. In this case, the content of methyl cellulose was 0.3 wt % based on the total weight of the ferrite-based catalyst, and the content of the ferrite-based catalyst was 15 wt % based on the total weight of the ferrite-based coating catalyst. In this case, the weight ratio of the introduced water was 0.1 or less based on the weight of the support.

The coated catalyst was dried under a temperature condition of 90° C. to 120° C. for several hours, and in order to remove the introduced methyl cellulose, the dried catalyst was put into a firing furnace and heat-treated at 650° C. for 6 hours to perform a firing step.

Example 2

A ferrite-based coating catalyst was prepared in the same manner as in Example 1, except that hydroxypropylmethylcellulose was used instead of the methyl cellulose in Example 1.

Example 3

A ferrite-based coating catalyst was prepared in the same manner as in Example 1, except that methyl cellulose and water were mixed in advance, and then the resulting mixture was introduced into a coating machine instead of mixing the ferrite-based catalyst and the methyl cellulose in Example 1.

Example 4

A ferrite-based coating catalyst was prepared in the same manner as in Example 3, except that hydroxypropylmethylcellulose was used instead of the methyl cellulose in Example 3.

Example 5

A ferrite-based coating catalyst was prepared in the same manner as in Example 1, except that the content of the ferrite-based catalyst was adjusted to 25 wt % based on the total weight of the ferrite-based coating catalyst in Example 1.

Example 6

A ferrite-based coating catalyst was prepared in the same manner as in Example 1, except that the content of the ferrite-based catalyst was adjusted to 35 wt % based on the total weight of the ferrite-based coating catalyst in Example 1.

Example 7

A ferrite-based coating catalyst was prepared in the same manner as in Example 5, except that the content of the methyl cellulose was adjusted to 0.05 wt % based on the total weight of the ferrite-based catalyst in Example 5.

Example 8

A ferrite-based coating catalyst was prepared in the same manner as in Example 5, except that the content of the methyl cellulose was adjusted to 0.01 wt % based on the total weight of the ferrite-based catalyst in Example 5.

Comparative Example 1

A ferrite-based coating catalyst was prepared in the same manner as in Example 1, except that the methyl cellulose was not used in Example 1.

Comparative Example 2

A ferrite-based coating catalyst was prepared in the same manner as in Example 5, except that the methyl cellulose was not used in Example 5.

Comparative Example 3

A ferrite-based coating catalyst was prepared in the same manner as in Example 6, except that the methyl cellulose was not used in Example 6.

Comparative Example 4

A ferrite-based coating catalyst was prepared in the same manner as in Example 5, except that the content of the methyl cellulose was adjusted to 1.0 wt % based on the total weight of the ferrite-based catalyst in Example 5.

Experimental Example

As reactants, a mixture of trans-2-butene and cis-2-butene and oxygen were used, and nitrogen and stem were additionally allowed to flow into a reactor together. For the reaction composition, the volume ratios of oxygen, nitrogen, and steam based on butene were 1, 4, and 5, respectively, and the butene was composed such that the component ratios of trans-2-butene and cis-2-butene were 60% and 40% by volume, respectively. The reaction was performed under the conditions of 400° C., GHSV=66 h$^{-1}$, OBR=1, SBR=8, and NBR=1. As the reactor, a metal tubular fixed bed reactor was used. The fixed bed reactor was filled with 200 cc of each of the catalysts prepared in the Examples and the Comparative Examples, steam was infused in the form of water, the water was vaporized into steam at 120° C. by using a vaporizer, the steam was mixed with the butene mixture and oxygen as the reactants, and the resulting mixture was allowed to flow into the reactor. The product after the reaction was analyzed by using gas chromatography (GC), and the conversion of butene, the selectivity of butadiene, the selectivity of COx, and the yield were calculated by using the results measured by gas chromatography.

GHSV: Gas Hourly Space Velocity
OBR: O$_2$/butene molar ratio
SBR: Steam/butene molar ratio
NBR: N$_2$/butene molar ratio The degree of the catalyst lost was evaluated by using an attrition test device in the following FIG. 1, and the results are shown in the following Table 1. More specifically, the rate of catalyst lost was calculated by putting the prepared coating catalyst into the attrition test device, rotating the device at a rate of 90 rpm for 5 minutes, and measuring the masses before and after the experiment.

TABLE 1

| Type of catalyst | Catalyst loss (wt %) |
| --- | --- |
| Example 1 | 3.5 |
| Example 2 | 6.8 |
| Example 3 | 3.5 |
| Example 4 | 5.1 |
| Example 5 | 0.7 |
| Example 6 | 1.4 |
| Example 7 | 0.7 |
| Example 8 | 5.7 |
| Comparative Example 1 | 33.6 |
| Comparative Example 2 | 37.2 |
| Comparative Example 3 | 40.8 |
| Comparative Example 4 | 0.7 |

Further, the results of calculating the conversion of butene, the selectivity of butadiene, and the like by using GC equipment are shown in the following Table 2.

TABLE 2

| Type of catalyst | Reaction temperature (° C.) | Hot spot temperature (° C.) | Conversion of butane (%) | Selectivity of butadiene (%) | Yield of butadiene (%) | Selectivity of COx (%) |
| --- | --- | --- | --- | --- | --- | --- |
| Example 8 | 321 | 478 | 83.4 | 84.8 | 70.7 | 12.5 |
| Comparative Example 2 | 321 | 483 | 82.7 | 86.6 | 71.6 | 12.0 |
| Comparative Example 4 | 321 | 493 | 78.5 | 84.2 | 66.1 | 14.3 |

As in the results, in an exemplary embodiment of the present application, it can be confirmed that the attrition property is improved regardless of the form and type of cellulose-based additive by introducing the cellulose-based additive during the preparation of the ferrite-based coating catalyst.

Furthermore, the ferrite-based coating catalyst according to an exemplary embodiment of the present application had a catalytic activity equivalent to those of the catalysts in the related art. In particular, it can be confirmed that in Comparative Example 4, the cellulose-based additive is introduced in excess, and as a result, the strength of the catalyst is improved, but the activity of the catalyst is reduced. Accordingly, by adjusting the content of the cellulose-based additive to 0.5 wt % or less based on the total weight of the ferrite-based catalyst during the preparation of the ferrite-based coating catalyst as in the present application, it is possible to improve the catalyst strength while maintaining the catalytic activity of the ferrite-based coating catalyst.

Although the preferred exemplary embodiments of the present invention have been described above, the present invention is not limited thereto, and various modifications can be made and carried out within the scope of the claims and the detailed description of the invention, and also fall within the scope of the invention.

The invention claimed is:

1. A method for preparing a ferrite-based coating catalyst, the method comprising:
   mixing in a coating machine a support, a ferrite-based catalyst, a cellulose-based additive, and water to form a coated support,
   wherein:
   the support is an alumina in the form of a sphere,
   a ratio of a weight of the water to a weight of the support introduced into the coating machine is 0.01 to 0.1, and
   a content of the cellulose-based additive is 0.5 wt % or less based on a total weight of the ferrite-based catalyst.

2. The method of claim 1, wherein the cellulose-based additive comprises one or more of methyl cellulose and hydroxypropylmethylcellulose.

3. The method of claim 1, wherein a content of the ferrite-based catalyst in the ferrite-based coating catalyst is 10 wt % to 40 wt % based on a total weight of the ferrite-based coating catalyst.

4. The method of claim 1, wherein the mixing comprises mixing the support, the ferrite-based catalyst, and the cellulose-based additive to form a resulting mixture, and then mixing the resulting mixture with the water.

5. The method of claim 1, wherein the mixing comprises mixing the cellulose-based additive and the water to form a resulting mixture, and then mixing the resulting mixture with the support and the ferrite-based catalyst.

6. The method of claim 1, wherein the ferrite-based catalyst is a compound of Formula 1:

$$AFe_2O_4 \qquad \text{Formula 1}$$

in Formula 1, A is Cu, Ra, Ba, Sr, Ca, Be, Zn, Mg, Mn, Co, or Ni.

7. The method of claim 1, wherein the support further comprises one or more of silica, cordierite, titania, zirconia, silicon nitride, and silicon carbide.

8. The method of claim 1, further comprising: drying the resulting mixture after the mixing of the support, the ferrite-based catalyst, the cellulose-based additive, and the water.

9. The method of claim 8, wherein the drying is performed at room temperature or at a temperature of 50° C. to 150° C.

10. The method of claim 8, further comprising firing the dried mixture at a temperature of 650° C.

11. The method of claim 1, wherein the support comprises alumina in a form of a sphere having a diameter of 2 mm to 7 mm.

12. A method for preparing butadiene, the method comprising:
   preparing a ferrite-based coating catalyst prepared by the preparation method of claim 1; and
   preparing butadiene by using the ferrite-based coating catalyst in an oxidative dehydrogenation reaction of butene.

* * * * *